US012564421B2

(12) United States Patent
Oppegard et al.

(10) Patent No.: US 12,564,421 B2
(45) Date of Patent: Mar. 3, 2026

(54) PERITONEAL TROCAR APPARATUS AND SYSTEM

(71) Applicants: Baxter International Inc., Deerfield, IL (US); Baxter Healthcare SA, Glattpark (CH); Mayo Foundation for Medical Education and Research, Rochester, MN (US)

(72) Inventors: Shawn Collin Oppegard, Fox River Grove, IL (US); Unberto Garcia, Bellwood, IL (US); Carlos Alberto Corrales Nogales, Vernon Hills, IL (US); Jorge Del Castillo, Des Plaines, IL (US); Jeshrene Enerio, Glenview, IL (US); Brian Connell, Evanston, IL (US); Steven Bowers, Ponte Vendra Beach, FL (US); Ivan E. Porter, II, Jacksonville, FL (US); Charles Ritchie, Ponte Vedra, FL (US)

(73) Assignees: Baxter International Inc., Deerfield, IL (US); Baxter Healthcare SA, Glattpark (CH); Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 17/666,838

(22) Filed: Feb. 8, 2022

(65) Prior Publication Data

US 2022/0249124 A1 Aug. 11, 2022

Related U.S. Application Data

(60) Provisional application No. 63/147,445, filed on Feb. 9, 2021.

(51) Int. Cl.
*A61B 17/34* (2006.01)
*A61B 17/00* (2006.01)
(Continued)

(52) U.S. Cl.
CPC ...... *A61B 17/3415* (2013.01); *A61B 17/3417* (2013.01); *A61M 13/003* (2013.01);
(Continued)

(58) Field of Classification Search
CPC ................ A61M 13/003; A61M 1/285; A61M 2205/3344; A61M 2205/75; A61M 39/02;
(Continued)

(56) References Cited

U.S. PATENT DOCUMENTS

| | | | | | |
|---|---|---|---|---|---|
| 5,762,629 | A | * | 6/1998 | Kambin | ............. A61B 17/3421 604/524 |
| 5,820,600 | A | * | 10/1998 | Carlson | ............. A61B 17/3462 604/167.03 |

(Continued)

OTHER PUBLICATIONS ip.com, "Dual Lumen Trocar for Intra-Operative Use of Ancillary Devices" An IP.com Prior Art Database Technical Disclosure, IP.com No. IPCOM000239150D, IP.com Electronic Publication Date: Oct. 16, 2014—2 pages.

*Primary Examiner* — Kami A Bosworth
*Assistant Examiner* — Avery Smale
(74) *Attorney, Agent, or Firm* — K&L Gates LLP

(57) ABSTRACT

A trocar for peritoneal dialysis is disclosed herein. An example trocar includes a conduit having two parallel lumens and a head connected to a first end of the conduit. The head includes two parallel lumens that are aligned respectively with the two parallel lumens of the conduit. The trocar also includes a coupler connected to the head. The coupler includes two (or more) parallel lumens that are aligned respectively with the two parallel lumens of the head. The coupler includes a coupling mechanism for securing surgical tools in place after insertion into a patient. The trocar may also include an obturator having a shaft that is removably inserted through the coupler, the head, and the conduit to protrude from a second end of the conduit.

14 Claims, 11 Drawing Sheets

(51) Int. Cl.
     A61M 13/00          (2006.01)
     A61M 39/02          (2006.01)

(52) U.S. Cl.
     CPC ...  *A61M 39/02* (2013.01); *A61B 2017/00477*
              (2013.01); *A61B 2017/3419* (2013.01); *A61B*
                                    *2017/347* (2013.01)

(58) Field of Classification Search
     CPC ...... A61M 39/0247; A61M 2039/0264; A61M
                2039/027; A61M 2039/0279; A61M
              13/00; A61M 13/006; A61B 17/34; A61B
              17/3415; A61B 17/3417; A61B 17/3474;
                   A61B 2017/00477; A61B 2017/3419;
                                    A61B 2017/347
     See application file for complete search history.

(56)                    References Cited

U.S. PATENT DOCUMENTS

|  |  |  |  |
|---|---|---|---|
| 7,938,793 B2 | 5/2011 | Mantell | |
| 10,758,262 B2 | 9/2020 | Bonde et al. | |
| 2005/0077689 A1* | 4/2005 | Hueil ................. | A61B 17/3421 |
| | | | 277/628 |
| 2009/0076464 A1* | 3/2009 | Gresham ............ | A61B 17/3498 |
| | | | 600/184 |
| 2011/0054261 A1* | 3/2011 | Battles .............. | A61B 17/3462 |
| | | | 600/210 |
| 2011/0313250 A1* | 12/2011 | Kleyman ........... | A61B 17/3423 |
| | | | 600/123 |
| 2016/0270816 A1* | 9/2016 | Mather ................. | A61B 90/30 |
| 2017/0027607 A1* | 2/2017 | Verbeek ............ | A61B 17/3421 |
| 2018/0132895 A1 | 5/2018 | Silver | |
| 2018/0168743 A1* | 6/2018 | Schmid ................ | A61B 34/70 |

* cited by examiner

500

| Conduit End | Lumen | Lumen Wall | Head Seal | Coupler | Surgical Tool | Obturator End | Obturator Shaft |
|---|---|---|---|---|---|---|---|
| Beveled | One | Rigid | No seal | Luer | Catheter | Sharp Point | Single |
| Straight | Two | Flexible Membrane | Pinhole | Locking Threads | Endoscope | Sharp Blade | Dual |
|  | Three |  | Cross-Slits | Twist-Lock | Fluid Aspiration System | Dilating | Triple |
|  | Four |  |  | Compression Twist | Electro-Surgery Tool | Blunt |  |
|  |  |  |  | Ratcheting | Insufflation Needle |  |  |
|  |  |  |  | Quick-Release Latch | Laparoscopic Tool |  |  |

FIG. 5

PERITONEAL TROCAR APPARATUS AND SYSTEM

PRIORITY CLAIM

This application claims priority to and the benefit as a non-provisional application of U.S. Provisional Patent Application No. 63/147,445 filed Feb. 9, 2021, the entire contents of which are hereby incorporated by reference and relied upon.

BACKGROUND

Due to various causes, a person's renal system can fail. Renal failure produces several physiological derangements. For instance, it is no longer possible for a person with renal failure to balance water and minerals or to excrete daily metabolic load. Additionally, toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is peritoneal dialysis ("PD"), which infuses a dialysis solution, also called dialysis fluid or PD fluid, into a patient's peritoneal cavity via a catheter. The dialysis fluid contacts a peritoneal membrane in a patient's peritoneal cavity. Waste, toxins and excess water pass from the patient's bloodstream, through the capillaries in the peritoneal membrane, and into the dialysis fluid due to diffusion and osmosis (i.e., an osmotic gradient occurs across the membrane). An osmotic agent in the dialysis fluid provides the osmotic gradient. Used or spent dialysis fluid is drained from the patient, removing waste, toxins, and excess water from the patient. This cycle is repeated multiple times.

There are various types of peritoneal dialysis therapies, including continuous ambulatory peritoneal dialysis ("CAPD"), automated peritoneal dialysis ("APD"), tidal flow dialysis, and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, where the transfer of waste, toxins, and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, a source or bag of fresh dialysis fluid, and a fluid drain. APD machines pump fresh dialysis fluid from a dialysis fluid source, through the catheter, and into the patient's peritoneal cavity. APD machines also allow for the dialysis fluid to dwell within the chamber and for the transfer of waste, toxins, and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal cavity of the patient until the start of the next treatment, or may be manually emptied at some point during the day.

For PD, a catheter is often inserted into a patient's peritoneal cavity using a trocar, which includes an obturator and a lumen. After initial placement of the trocar, the obturator is removed and replaced with a catheter. After the catheter is inserted and placed by a clinician, the trocar is removed leaving the catheter in place.

Oftentimes, multiple trocars are used to provide multiple portals for the placement of different surgical tools. For instance, a second trocar may be inserted into a patient to enable the use of tools for aligning a catheter in the patient's peritoneal cavity. Other trocars may be used to provide access for a camera, an insufflation tool, or a port to enable smoke/gas evacuation. The use of multiple trocars (or multiple surgical tools at different locations) means that a patient is punctured in multiple locations. The multiple punctures increase the chances of infection at the insertion site and/or increase the chances of peritoneal fluid leakage in the event an insertion site is not adequately closed. Further, the use of multiple insertion sites may increase patient discomfort during catheter placement and afterwards during healing.

A need accordingly exists for improved trocars and methods of using trocars to reduce a number of insertion sites during a medical procedure, such as catheter placement or insufflation.

SUMMARY

An improved trocar is disclosed herein for providing access to a patient's peritoneal cavity for placement of a peritoneal dialysis catheter. The example trocar includes multiple lumens to accommodate different surgical tools. The example trocar also includes a coupler having coupling mechanisms to lock the different tools in place as needed during a surgical procedure. The use of a single trocar with multiple lumens reduces the number of insertion points on a patient, thereby improving patient healing.

In one example, the trocar includes a first lumen that enables a peritoneal dialysis catheter to be inserted into a peritoneal cavity of a patient. The trocar also includes a second lumen that enables a laparoscope/endoscope to pass through. The laparoscope/endoscope provides direct visualization of the catheter during insertion. The direct visualization enables a clinician to more easily position a catheter in a desired position without having to create a second incision into the patient's peritoneal cavity.

In another example, an insufflation needle is first placed into one of the lumens of the trocar. Insertion of the insufflation needle enables expansion of the patient's peritoneal wall via a compressed gas, thereby increasing a size of the peritoneal cavity. After insufflation has ended, the needle may be removed from the trocar. As disclosed herein, the trocar includes one or more gaskets or seals to prevent depressurization of the peritoneal cavity after the insufflation needle has been removed. The catheter may then be inserted into the patient via the same trocar lumen. The multi-lumen trocar in this example enables patient insufflation, endoscopic visualization of the peritoneal cavity, and catheter placement through a single incision location on the patient.

The example trocar disclosed herein may include a removable obturator. In embodiments where the obturator includes a single shaft, the trocar may include a flexible membrane that separates the two lumens. Insertion of the obturator into one of the trocar lumens causes the flexible membrane to expand into the other lumen. The obturator may have a wide diameter that completely closes the other lumen to prevent tissue from entering the trocar during insertion into a patient's peritoneal cavity.

In some embodiments, the trocar may be used with a low-cost insufflation device. As disclosed herein the insufflation device is configured to accept removable (and portable) compressed gas containers. The insufflation device includes one or more pressure regulators and a compliance chamber to reduce or eliminate pressure fluctuations or over pressurization scenarios. The compliance chamber is connected via a tube to an insufflation needle. The relatively efficient insufflation device enables use outside of hospital settings or in regions that do not have access to expensive insufflation machines or central compressed gas sources. In some embodiments, the insufflation device may alternatively or additionally include a connection to an external compressed gas source (such as a compressed gas source of a medical facility) to enable flexible use.

In light of the disclosure set forth herein, and without limiting the disclosure in any way, in a first aspect of the present disclosure, which may be combined with any other aspect, or portion thereof, described herein a trocar apparatus includes a conduit having two parallel conduit lumens, the conduit including a first end and a second end. The trocar apparatus also includes a head connected the first end of the conduit. The head includes two parallel head lumens that are aligned respectively with the two parallel conduit lumens. The head has a width that is greater than a width of the conduit to prevent the trocar from slipping into a patient at an insertion location. The head includes at least one of a gasket or seal for each head lumen. The trocar apparatus further includes a coupler connected to the head. The coupler includes two parallel coupler lumens that are aligned respectively with the two parallel head lumens. The coupler also includes a coupling mechanism for each coupler lumen. Additionally, the trocar apparatus includes an obturator having a shaft that is removably inserted through one of the coupling mechanisms and through the respective coupler lumen, head lumen, and conduit lumen. The obturator includes an end that is configured to protrude from the second end of the conduit.

In a second aspect of the present disclosure, which may be combined with any other aspect, or portion thereof, described herein, the obturator includes two parallel shafts that are inserted respectively through the coupling mechanisms of the coupler and through the respective coupler lumens, head lumens, and conduit lumens.

In a third aspect of the present disclosure, which may be combined with any other aspect, or portion thereof, described herein, the end of the obturator includes at least one of a sharp point, a sharp blade, a blunt tip, or a dilation tip for puncturing into a peritoneal cavity of the patient at the insertion location of the patient.

In a fourth aspect of the present disclosure, which may be combined with any other aspect, or portion thereof, described herein, the obturator is configured for removal from the trocar after insertion of the trocar into the peritoneal cavity.

In a fifth aspect of the present disclosure, which may be combined with any other aspect, or portion thereof, described herein, at least one of the conduit lumens or the head lumens are separated from each other via a flexible membrane wall.

In a sixth aspect of the present disclosure, which may be combined with any other aspect, or portion thereof, described herein, the obturator is configured to press against the flexible membrane wall when the obturator shaft is inserted through the respective coupler lumen, head lumen, and conduit lumen causing the flexible membrane wall to close or reduce a width of the other of the head lumen and the conduit lumen.

In a seventh aspect of the present disclosure, which may be combined with any other aspect, or portion thereof, described herein, each coupling mechanism of the coupler includes at least one of an elastomeric gasket or seal.

In an eighth aspect of the present disclosure, which may be combined with any other aspect, or portion thereof, described herein, each coupling mechanism of the coupler includes a locking mechanism that secures a surgical tool to the trocar.

In a ninth aspect of the present disclosure, which may be combined with any other aspect, or portion thereof, described herein, the surgical tool includes at least one of an insufflation tool, an endoscope, a fluid aspiration tool, an electro-surgery device, a laparoscopic manipulator tool, or a catheter.

In a tenth aspect of the present disclosure, which may be combined with any other aspect, or portion thereof, described herein, each of the locking mechanisms includes at least one of a luer interface, locking threads, a twist-to-lock interface with a pin and slot, a compression twist fit, a ratcheting mechanism, or a quick-release latch.

In an eleventh aspect of the present disclosure, which may be combined with any other aspect, or portion thereof, described herein, the width of the conduit is between 3 millimeters ("mm") and 15 mm, the width of the head is between 8 mm and 50 mm, and a thickness of a wall of the conduit is between 0.1 mm and 0.8 mm.

In a twelfth aspect of the present disclosure, which may be combined with any other aspect, or portion thereof, described herein, the conduit has a length between 5 centimeters ("cm") and 15 cm.

In a thirteenth aspect of the present disclosure, which may be combined with any other aspect, or portion thereof, described herein, a trocar apparatus includes a conduit having two parallel conduit lumens, the conduit including a first end and a second end. The trocar apparatus also includes a head connected around an exterior of the conduit at the first end and configured to prevent the trocar from slipping into a patient at an insertion location. The head includes at least one of a gasket or a seal for each conduit lumen. Additionally, the trocar apparatus includes a coupler connected to the head. The coupler includes two parallel coupler lumens that are aligned respectively with the two parallel conduit lumens. The coupler includes a coupling mechanism for each coupler lumen. The trocar apparatus further includes an obturator having a shaft that is removably inserted through one of the coupling mechanisms and through the respective coupler lumen and conduit lumen. The obturator includes an end that is configured to protrude from the second end of the conduit.

In a fourteenth aspect of the present disclosure, which may be combined with any other aspect, or portion thereof, described herein, the conduit includes three parallel conduit lumens and the coupler includes three parallel coupler lumens that are aligned respectively with the three parallel conduit lumens, and wherein the coupler includes a coupling mechanism for each coupler lumen.

In a fifteenth aspect of the present disclosure, which may be combined with any other aspect, or portion thereof, described herein, each coupling mechanism of the coupler includes at least one of an elastomeric gasket or a seal.

In a sixteenth aspect of the present disclosure, which may be combined with any other aspect, or portion thereof, described herein, each coupling mechanism of the coupler includes a locking mechanism that secures a surgical tool to the trocar, and each of the locking mechanisms includes at least one of a luer interface, locking threads, a twist-to-lock interface with a pin and slot, a compression twist fit mechanism, a ratcheting mechanism, or a quick-release latch.

In a seventeenth aspect of the present disclosure, which may be combined with any other aspect, or portion thereof, described herein, one of the coupling mechanisms is configured to connect to a catheter and another of the coupling mechanisms is configured to connect to at least one of an insufflation tool or an endoscope.

In a eighteenth aspect of the present disclosure, which may be combined with any other aspect, or portion thereof, described herein, an insufflation apparatus includes a compressed gas container configured to hold a compressed gas, the compressed gas container including an outlet. The insufflation apparatus also includes a pressure regulator fluidly coupled to the outlet of the compressed gas container and a compliance chamber fluidly coupled to the pressure regulator via a first tube. The compliance chamber is configured to reduce pressure fluctuations of the compressed gas. The insufflation apparatus further includes an insufflation needle fluidly coupled to the compliance chamber via a second tube. The insufflation needle is configured for placement into a peritoneal cavity of a patient.

In a nineteenth aspect of the present disclosure, which may be combined with any other aspect, or portion thereof, described herein, the insufflation apparatus further includes a housing configured to enclose the compressed gas container, the pressure regulator, the compliance chamber, and the first tube.

In a twentieth aspect of the present disclosure, which may be combined with any other aspect, or portion thereof, described herein, the housing includes a door to enable replacement of the compressed gas cartridge.

In a twenty-first aspect of the present disclosure, which may be combined with any other aspect, or portion thereof, described herein, the insufflation apparatus further includes a first air filter fluidly coupled between the compliance chamber and the second tube and a second air filter fluidly coupled between the insufflation needle and the second tube.

In a twenty-second aspect of the present disclosure, which may be combined with any other aspect, or portion thereof, described herein, the pressure regulator is a first pressure regulator, the apparatus further includes a second pressure regulator fluidly connected to the second tube.

In a twenty-third aspect of the present disclosure, which may be combined with any other aspect, or portion thereof, described herein, the compressed gas container includes at least one of carbon dioxide, atmospheric air, nitrogen, or nitrous oxide.

In a twenty-fourth aspect, any of the features, functionality and alternatives described in connection with any one or more of FIGS. 1 to 9 may be combined with any of the features, functionality and alternatives described in connection with any other of FIGS. 1 to 9.

In light of the present disclosure and the above aspects, it is therefore an advantage of the present disclosure to provide a trocar with at least two parallel lumens to enable multiple surgical tools to be inserted through a single incision in a patient.

It is another advantage of the present disclosure to provide a trocar with a coupling mechanism to hold at least one surgical tool in place during a surgical procedure.

It is yet another advantage of the present disclosure to provide a portable insufflation device with at least one compressed gas cartridge and a compliance chamber to enable insufflation of a peritoneal cavity outside of hospital environments.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

BRIEF DESCRIPTION OF THE FIGURES

FIG. 5 is a table illustrating different configurations of the example trocar of FIGS. 1 to 4, according to an example embodiment of the present disclosure.

DETAILED DESCRIPTION

An example peritoneal dialysis trocar with at least two lumens is disclosed herein. The inclusion of multiple lumens in a trocar enables multiple surgical tools to be inserted into a patient's peritoneal cavity through a single incision location. The trocar reduces the number of incision locations on a patient for placement of a peritoneal dialysis catheter, which reduces the chances of infection and peritoneal fluid seepage. The reduced number of incision locations also improves patient healing, reduces cosmetic damage, and reduces patient discomfort during and after the placement of a catheter.

Known trocars contain only a single lumen for setting a catheter in a patient's peritoneal cavity. Separate incision locations are needed for insufflation and endoscopic visualization. Having separate incision locations increases the chances of infection and peritoneal fluid seepage. The multiple incision locations also reduce patient comfort during catheter placement and afterwards when peritoneal dialysis begins.

The example trocar is discussed herein with reference to peritoneal dialysis. It should appreciated that the trocar may be used for other medical applications in which multiple surgical tools can be inserted through a single patient insertion location. For example, the trocar may be used for gastric procedures, bladder procedures, lung procedures, etc.

Trocar Embodiment

Figure 1:
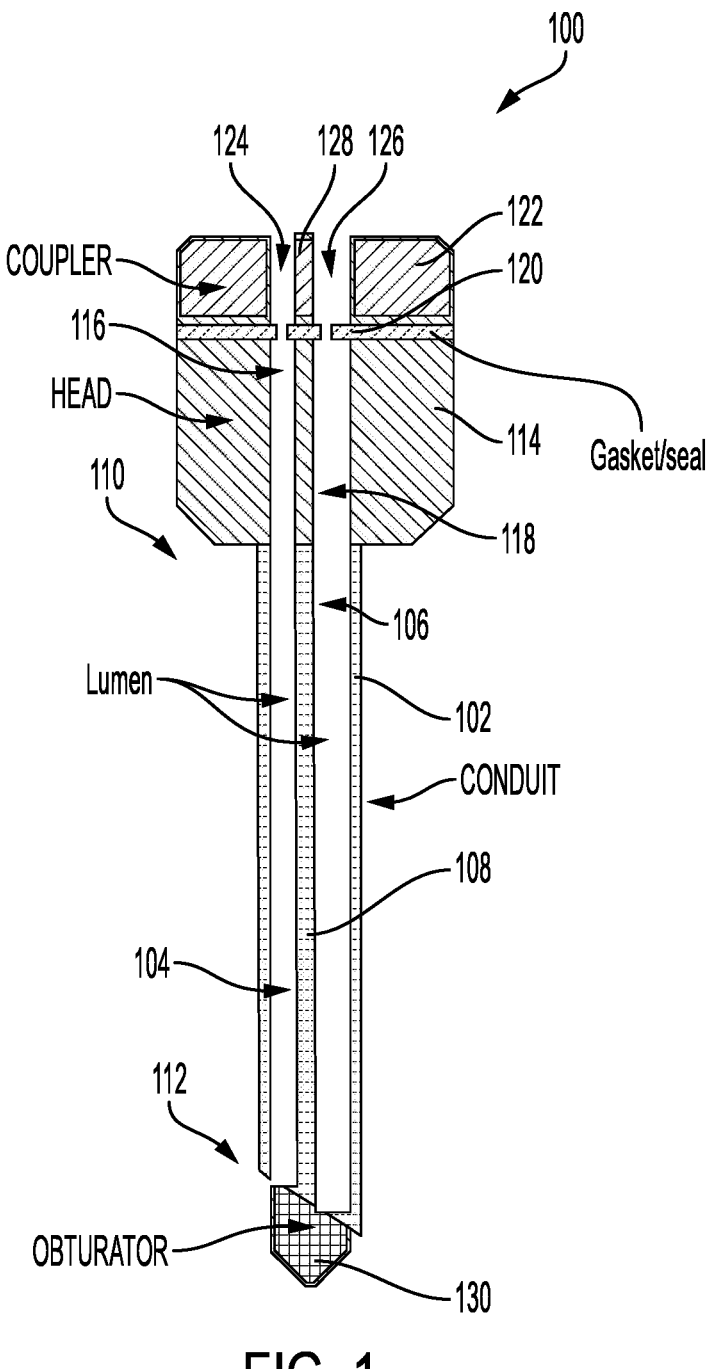
FIG. 1 is a diagram of a trocar including a conduit, head, and coupler, according to an example embodiment of the present disclosure.

FIG. 1 is a diagram of a trocar 100, according to an example embodiment of the present disclosure. The example trocar 100 is configured to provide a portal to a patient's peritoneal cavity through an incision. The trocar 100 includes a conduit 102 having a first lumen 104 and a parallel second lumen 106. In other examples, the conduit 102 may have three, four, or more parallel lumens.

The conduit 102 may be formed using any rigid material such as, for example, stainless steel, aluminum, polypropylene, or any other surgical grade metal, plastic, or combinations thereof. The conduit 102 may also comprise glass, surgical grade steel, etc. The conduit 102 has a width between 3 millimeters ("mm") and 15 mm and a length between 5 centimeters ("cm") and 15 cm. A wall of the conduit may have a thickness between 0.1 mm and 0.8 mm.

The conduit 102 may include a single channel that is separated into two parallel halves (forming the lumens 104 and 106). The separation may be provided by a rigid structure or a flexible membrane 108. Alternatively, the conduit 102 may be formed as two parallel channels comprising the lumens 104 and 106. While only two lumens are shown, in other embodiments the conduit 102 may include three or more parallel lumens. Each of the lumens may have a same width or diameter or different widths/diameters based on which surgical instrument is to pass through. For example, a lumen designated for insufflation may have a smaller width/diameter compared to lumens for a catheter, endoscope, and/or laparoscopic manipulation tool.

The example conduit 102 includes a first end 110 and a second end 112. The first end 110 of the conduit 102 is located away from a patient while the second end 112 is configured for insertion into a patient to enable the trocar 100 to spread and hold incised tissue. In the illustrated example, the second end 112 includes a beveled edge for minimizing placement depth in a patient's peritoneum during an angled insertion. In other examples, the second end 112 includes a straight edge. The beveled edge or straight edge may include a blunt tip or a sharp tip to help incise skin. If the second end 112 includes a blunt tip, a scalpel may be used to first create an incision into the peritoneum. A veress needle or a guidewire may instead be used to create an initial puncture for the conduit 102 of the trocar 100.

As shown in FIG. 1, the first end 110 of the conduit 102 is connected to a head 114, which is configured to prevent the trocar 100 from slipping or otherwise moving completely through an incision into the patient. The head 114 has a width or a diameter that is greater than a width or diameter of the conduit 102. For example, the width of the head 114 may be between 8 mm and 50 mm.

In the illustrated example, the head 114 includes a first lumen 116 and a parallel second lumen 118. The first lumen 116 is aligned with the lumen 104 of the conduit 102 and the second lumen 118 is aligned with the lumen 106 of the conduit 102. The alignment of the lumens 104, 106, 114 and 116 respectively provides for separation of surgical tools through the trocar 100.

In alternative embodiments, only the head 114 includes lumens 116 and 118. In these embodiments, the conduit 102 includes a single lumen. The dual lumens 116 and 118 in the head 114 provide sufficient separation of surgical tools such that multiple lumens in the conduit 102 are not needed. In yet alternative embodiments, the conduit 102 may include multiple lumens while the head 114 includes a single lumen or channel.

In some embodiments, the head 114 of the trocar 100 includes a closure mechanism 120, such as a gasket or a seal. The example closure mechanism 120 is configured to provide a seal to retain gas within the peritoneal cavity during procedures that require insufflation or pneumoperitoneum. The closure mechanism 120 may include a rubber, plastic, or other material that enables a surgical tool to pass through while retaining a fluidic seal. In instances where insufflation or pneumoperitoneum is not required, the closure mechanism 120 may be removed or omitted from the trocar 100.

The example closure mechanism 120 includes an aperture or opening for each lumen 116 and 118 of the head 114. In other instances, the closure mechanism 120 includes one or more pinhole openings for each lumen 116 and 118 and is flexible to mechanically seal around an inserted tool. In yet other instances, the closure mechanism 120 may include one or more cross slits for each lumen 116 and 118 to permit spreading with an inserted surgical tool. Additionally or alternatively, the closure mechanism 120 has a locking mechanism that is configured to loosen and tighten around inserted surgical tools. For instance, a locking mechanism may include a latch, a quick-release latch, button, and/or twisting actuator that enables an operator to tighten or loosen a grip of the closure mechanism 120 on a surgical tool.

While the closure mechanism 120 is shown as a single structure of material, in other embodiments a closure mechanism may be separately provided for each lumen 116 and 118 of the head 114. Further, while the closure mechanism 120 is shown as being included within the head 114, in other examples, the closure mechanism 120 may be included within the conduit 102 or a coupler 122 that is connected to the head 114. In some instances, the head 114 may include a closure mechanism 120 without a locking mechanism while the coupler 122 includes a second closure mechanism 120 with a locking mechanism. In alternative embodiments, the closure mechanism 120 may be located between the head 114 and the coupler 122.

The example coupler 122 of FIG. 1 is connected to the head 114. In some embodiments, the coupler 122 may be integrally formed with the head 114. The example coupler 122 is configured to provide a secure connection to one or more surgical tools during a procedure. The secure connection prevents the surgical tools from unwanted movement during a procedure. The coupler 122 includes a first lumen 124 and a parallel second lumen 126 for receiving surgical tools. The lumens 124 and 126 are aligned respectively with the lumens 116 and 118 of the head 114 to enable surgical tools to pass through the trocar 100. The lumens 124 and 126 may be separated by a wall or partition 128 to prevent surgical tools from contacting each other.

Figure 2:
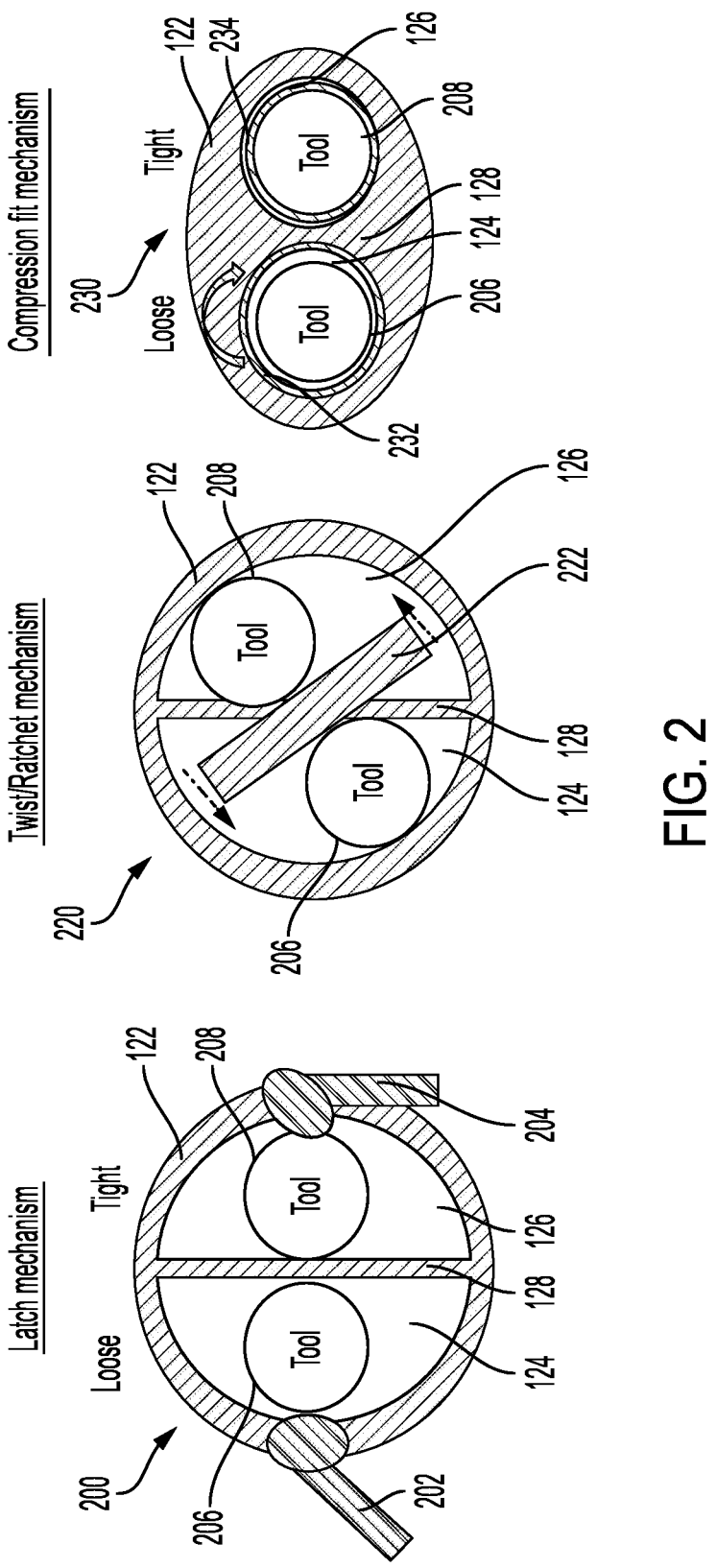
FIG. 2 shows diagrams of different types of locking/coupling mechanisms of the trocar coupler of FIG. 1, according to example embodiments of the present disclosure.

The coupler 122 may also include a locking mechanism and/or a coupling mechanism to provide a pneumatic seal and/or to reduce a risk of contamination during a procedure. FIG. 2 shows diagrams of different types of locking/coupling mechanisms of the coupler 122 of FIG. 1, according to example embodiments of the present disclosure. In one embodiment, the coupler 122 includes a latch locking mechanism 200. The example latch mechanism 200 includes a first latch 202 for the first lumen 124 and a second latch 204 for the second lumen 126. The latches 202 and 204 are positioned at a top or mid-section of the coupler 122.

The first latch 202 is configured to permit loosening or tightening with respect to a first surgical tool 206 while the second latch 204 is configured to permit loosening or tightening with respect to a second surgical tool 208. The first latch 202 is shown in a loosened position while the second latch 204 is shown in a tightened position. In a loosened position, the first latch 202 enables the surgical tool 206 to be moved vertically through the lumen 124 and/or horizontally around the lumen 124 by an operator. After the surgical tool 206 is set into a desired position, an operator moves the latch 202 to the closed position, causing the latch 202 to apply pressure against the surgical tool 206. The applied pressure provided by the latch 202 prevents the surgical tool 206 from moving vertically or horizontally. The rotation of the latch 202 to the closed position is configured to contact the tool 206 regardless of a position of the tool within the lumen 124. In some embodiments, the latches 202 and 204 may include quick-release latches. Alternatively, the latches may be replaced by buttons or other compression mechanisms.

In another embodiment, a locking mechanism 220 of the coupler 122 includes a ratchet mechanism 222. As shown in FIG. 2, the ratchet mechanism 222 includes a bar that is configured to rotate about a center of the coupler 122. Rotation, twisting, or sliding of the ratchet mechanism 222 causes the bar to press the surgical tools 206 and 208 against the wall 128 and outer walls of the lumens 124 and 126, thereby securing the surgical tools 206 and 208. The ratchet mechanism 222 may include teeth to hold the surgical tools 204 and 206 in a locked position. The ratchet mechanism 222 may include a release mechanism to unlock and enable positioning of the surgical tools 204 and 206. In some instances, the ratchet mechanism 222 aligns with the wall 128 in an unlock position.

In a further embodiment, a locking mechanism 230 of the coupler 122 includes compression twist fit connectors 232 and 234. A first connector 232 is provided with the first lumen 124 and a second connector 234 is provided with the second lumen 126. The first connector 232 is shown in an open or loosened position while the second connector 234 is shown in a closed or tight position. The connectors 232 and 234 are configured to be rotated clockwise to tighten and counter-clockwise to loosen. An operator may loosen the connectors 232 and 234 to position respective surgical tools 204 and 206. After positioning, the operator rotates the connectors 232 and 234 causing them to compress around the surgical tools 204 and 206 in the respective lumens 124 and 126, thereby locking the surgical tools in place. In some instances, the connectors 232 and 234 may provide a pneumatic seal when actuated to the closed position.

In other embodiments, the locking/coupling mechanism of the coupler 122 may include a luer interface similar to blood and dialysis sets or locking threads. Alternatively, the locking/coupling mechanism of the coupler 122 may include a twist-to-lock mechanism with a pin and slot. The coupler 122 shown in FIGS. 1 and 2 may include a gasket or other seal in conjunction with the locking/coupling mechanism. For example, a locking/coupling mechanism may be located at a top or mid-section of the coupler 122 while a gasket or a seal is provided at a lower section of the coupler 122 closer to the head 114.

In some embodiments, the coupler 122 may include a side extension with a third lumen configured to accept an insufflation tool. The inclusion of a side extension enables the insufflation tool to be placed through the trocar 100 without interfering with other surgical tools 204 and 206 that are placed through a top of the coupler 122. Further, the coupler 122 may be positioned between the head 114 and the conduit 102.

In addition to the embodiments above, the coupler 122 of FIGS. 1 and 2 may include an on/off valve to permit an operator to control a gas or liquid into a peritoneal cavity of a patient. Alternatively, the coupler 122 may include a one-way input valve that enables gas or fluid to flow into the peritoneal cavity. In this alternative embodiment, the coupler 122 may include a separate vent valve to prevent hyper pneumoperitoneum.

Returning to FIG. 1, the trocar 100 also includes a removable obturator 130. The example obturator 130 may be placed into the trocar 100 during initial insertion into a peritoneal cavity of a patient to prevent patient fluid/tissue from entering into the conduit 102. The obturator 130 may be placed through a lumen 124 or 126 of the coupler 122, and a respective lumen 116 or 118 of the head 114. A locking/coupling mechanism of the coupler 122, described above, may secure the obturator 130 in place. In some embodiments, the obturator 130 passes through one of the lumens 104 and 106 of the conduit 102 such that an end of the obturator extends from the conduit 102. To fully seal the conduit 102, the obturator 130 may press against the wall or membrane 108 of the conduit 102, thereby closing a second lumen.

Figure 3:
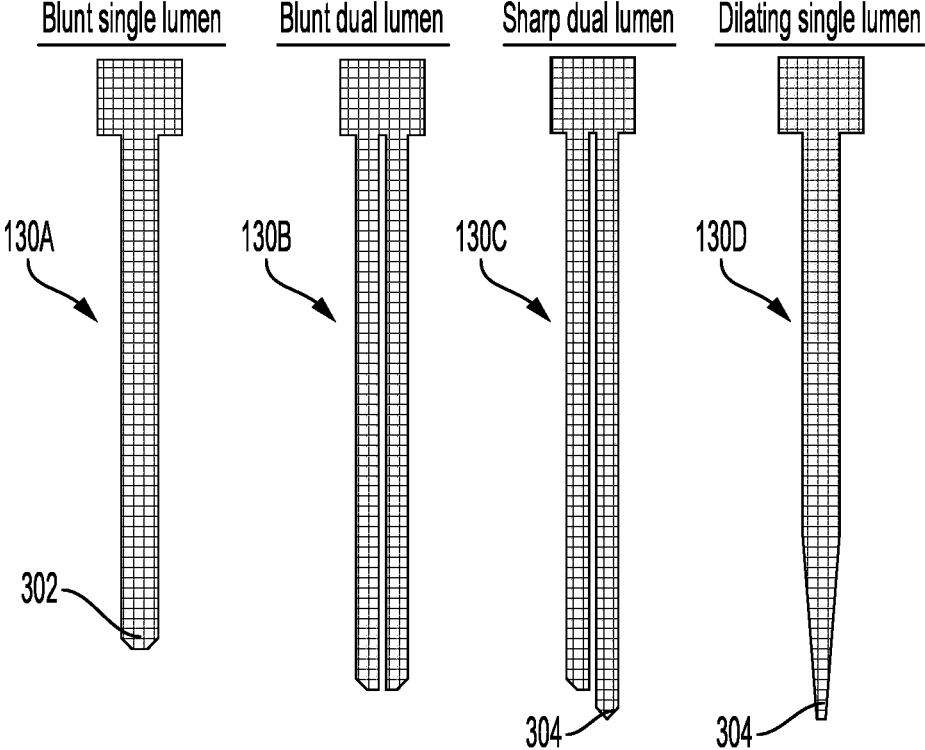
FIG. 3 shows diagrams of different types of trocar obturators, according to example embodiments of the present disclosure.

FIG. 3 shows diagrams of different types of obturators 130, according to example embodiments of the present disclosure. A first obturator 130A includes a single lumen and a blunt tip 302. If the first obturator 130A is used with the trocar 100, a separate tool is needed to make a surgical incision into a patient. A second obturator 130B includes two lumens, each having a blunt tip. Each of the lumens may slide through respective lumens of the conduit 102, head 114, and/or coupler 122.

A third obturator 130C includes two lumens having sharp tips 304. The tips 304 may include a sharp point and/or blade for piercing a patient's skin and underlying tissue. As shown in FIG. 3, the separate lumens may have different lengths to enable the longer lumen to first puncture the skin followed by the shorter lumen to increase a diameter of the puncture as the longer lumen progresses further into the skin/tissue.

A fourth obturator 130D includes a single lumen having a sharp tip 304. The tip of the obturator 130D is tapered to increase in diameter from a sharp point to a diameter of the conduit 102 of the trocar 100. The taper gradually increases a diameter of a puncture site as the obturator 130D and trocar 100 are inserted into a patient.

Trocar Surgical Use Embodiment

Figure 4:
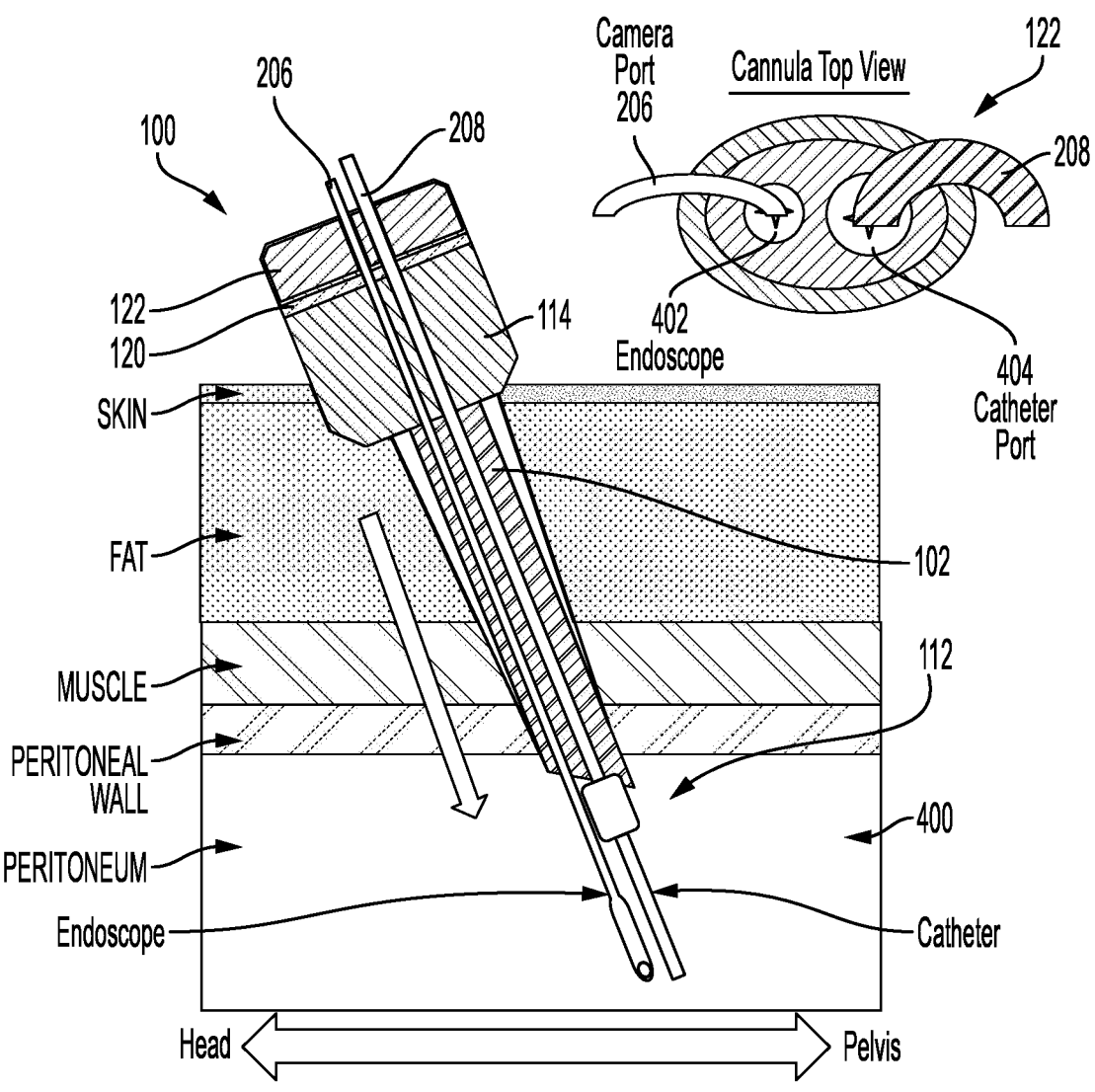
FIG. 4 is a diagram of the trocar of FIGS. 1 to 3 inserted into a peritoneal cavity of a patient, according to an example embodiment of the present disclosure.

FIG. 4 is a diagram of the trocar 100 of FIGS. 1 to 3 inserted into a peritoneal cavity 400 of a patient, according to an example embodiment of the present disclosure. In the illustrated example, the second end 112 of the conduit 102 of the trocar 100 is located in the peritoneal cavity 400. The conduit 102 passes through a peritoneal wall, muscle, fat, and skin of the patient. Additionally, the head 114 is placed against the skin to prevent the trocar 100 from falling completely into the peritoneal cavity 400.

In the illustrated example, the obturator 130 has been removed and surgical instruments 206 and 208 have been inserted into respective lumens of the conduit 102, the head 114, and the coupler 122. The first surgical instrument 206 includes an endoscope and the second surgical instrument 208 includes a catheter. In other embodiments, the surgical instruments can include an insufflation tool, a fluid aspiration tool, an electro-surgery device, a laparoscopic manipulator tool, etc.

FIG. 4 also shows a plan view of the coupler 122 of the trocar 100. The coupler 122 includes a first locking/coupling mechanism 402 adapted to receive the endoscope surgical tool 206 and a second locking/coupling mechanism 404 adapted to receive the catheter surgical tool 208. The locking/coupling mechanisms 402 and 404 include a seal or a gasket to prevent gas or fluid escape from the peritoneal cavity 400. In the illustrated embodiment, the locking/coupling mechanisms 402 and 404 have different diameters to correspond to the different diameters of the endoscope surgical tool 206 and the catheter surgical tool 208. In other embodiments, the diameters of the locking/coupling mechanisms 402 and 404 may be the same.

FIG. 5 is a table 500 illustrating different configurations of the example trocar 100 of FIGS. 1 to 4, according to an example embodiment of the present disclosure. It should be appreciated that the different configurations are interchangeable. As discussed above, the conduit 102 may have a beveled or straight end. Further, the conduit 102 may include one, two, three, four, or more lumens. The head 114 and coupler 122 may also include two, three, four, or more lumens. The conduit 102 may include a rigid or a flexible membrane separating the lumens.

Also, as shown in the table 500, the closure mechanism 120 of the head 114 may include a pinhole seal or cross-slits. Alternatively, the head 114 may not include a closure mechanism 120. The locking/coupling mechanism 402 and 404 of the coupler 122 may include a luer, locking threads, a twist-lock, a compression twist mechanism, a ratchet mechanism, or a latch. The coupler 122 may be adapted to accept a catheter, an endoscope, a fluid aspiration system, an electro-surgery tool, an insufflation needle, and/or a laparoscopic tool. Further, the obturator 130 may include a single, dual, or triple lumen and have a sharp point, a sharp blade, a dilating end, or a blunt end. The example trocar 100 disclosed herein enables multiple tools to be inserted into a patient's peritoneal cavity through a single incision, thereby improving patient comfort and health.

Figure 6:
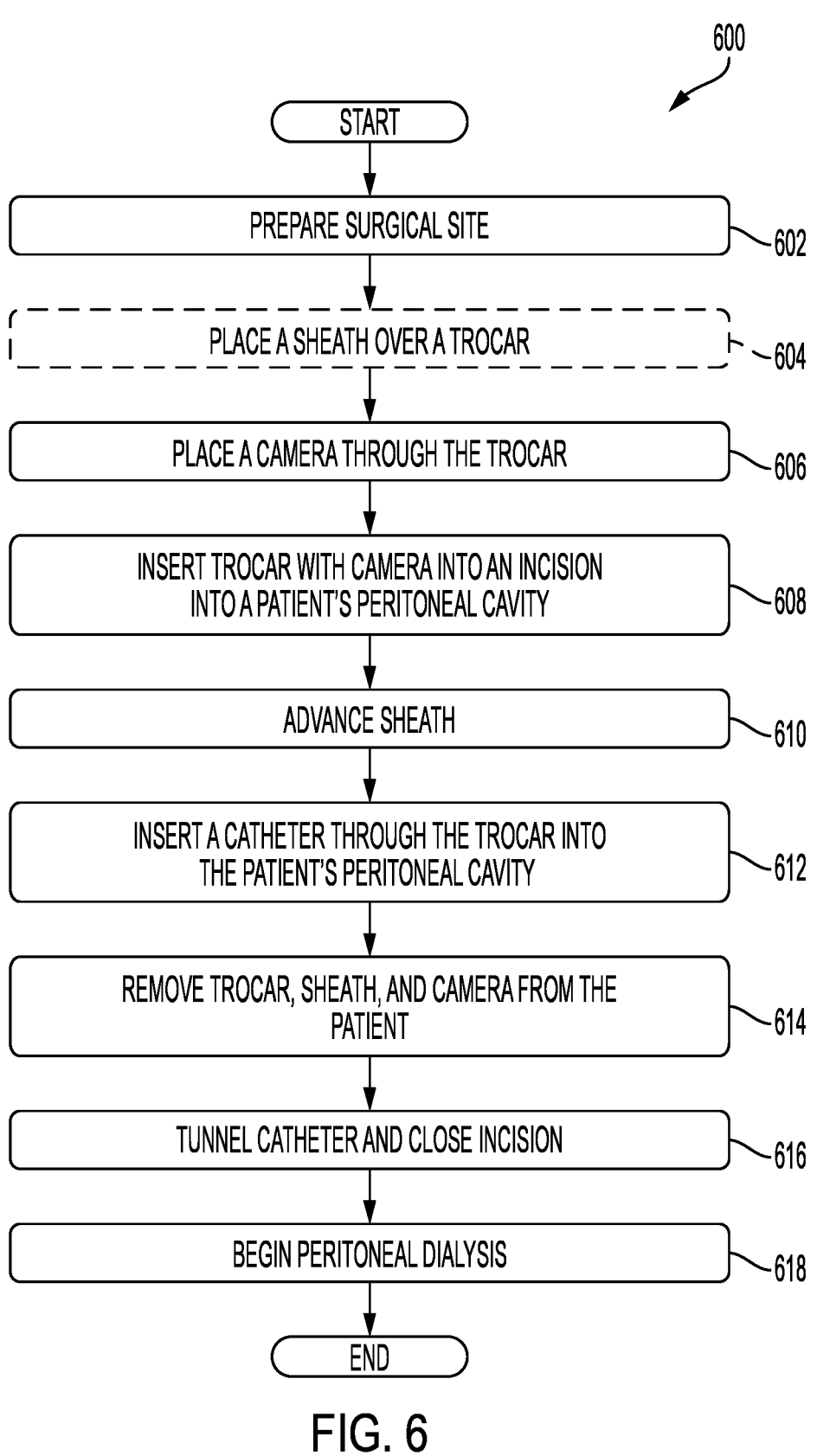
FIG. 6 is a diagram of an example procedure for inserting the trocar of FIGS. 1 to 5 within a peritoneal cavity of a patient for peritoneal dialysis, according to an example embodiment of the present disclosure.

FIG. 6 is a diagram of an example procedure 600 for inserting the trocar 100 of FIGS. 1 to 5 within a peritoneal cavity of a patient, according to an example embodiment of the present disclosure. Although the procedure 600 is described with reference to the flow diagram illustrated in FIG. 6, it should be appreciated that many other methods of performing the steps associated with the procedure 600 may be used. For example, the order of many of the blocks may be changed, certain blocks may be combined with other blocks, and many of the blocks described may be optional. In an embodiment, the number of blocks may be changed. For example, different steps may be performed based on which surgical tools are placed within the trocar 100. The example procedure 600 enables catheter placement for peritoneal dialysis with direct camera visualization to minimize the chance of a bowel injury. The use of the example trocar 100 in the example procedure 600 eliminates the need for an extensive surgical procedure and instead could be performed at a patient's bedside.

The example procedure 600 begins when a surgical site of a patient is prepared (block 602). Preparation includes sterilization of the patient's abdomen and anesthetization with lidocaine. Additionally, a veress needle may be inserted into the patient's peritoneal cavity to provide for insufflation. In other embodiments, insufflation may occur after the trocar 100 has been placed.

Figure 7A:
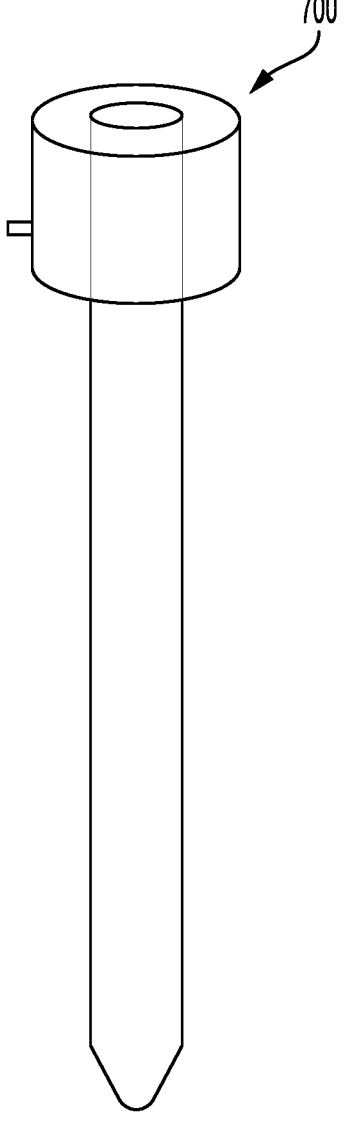
FIG. 7A shows a diagram of a peel-away sheath that may be placed over the trocar of FIGS. 1 to 5, according to an example embodiment of the present disclosure.

Next, a sheath may be placed over the trocar 100 (block 604). FIG. 7A shows a diagram of a peel-away sheath 700 that may be placed over the trocar 100. The sheath 700 may be used instead of an obturator 130 in instances where a surgical tool, such as a camera, in placed into the trocar 100 during insertion. The sheath 700 may be peelable to enable surgical tools to advance from the trocar 100 into the patient's peritoneal cavity. After the sheath 700 is in place, a camera or endoscope is placed into the trocar 100 through the coupler 122 (block 606). A locking/coupling mechanism of the coupler 122 retains the camera in place with the trocar 100.

The example procedure 600 continues by creating an incision at the surgical site on the patient's abdomen and advancing the trocar 100 with sheath 700 through the incision (block 608). The trocar 100 is advanced until the peritoneal cavity is reached. The sheath 700 may then be advanced or otherwise peeled to enable the camera to be advanced (block 610). After the camera is in place, a peritoneal catheter is inserted through the trocar 100 into the patient's peritoneal cavity (block 612). The camera provides direct visualization of the peritoneal cavity to enable an operator to position the catheter as desired without puncturing a patient's internal tissue. After catheter placement, a retention suture may be applied and/or retrorectus tunnel procedure may be performed.

The trocar 100, including the camera and the sheath 700, is then removed from the peritoneal cavity, thereby leaving the catheter in place (block 614). The catheter may be tunneled and the incision to the peritoneal cavity is closed (block 616). At this point, the catheter may be used to perform peritoneal dialysis (block 618). The example procedure 600 then ends.

Figure 7B:
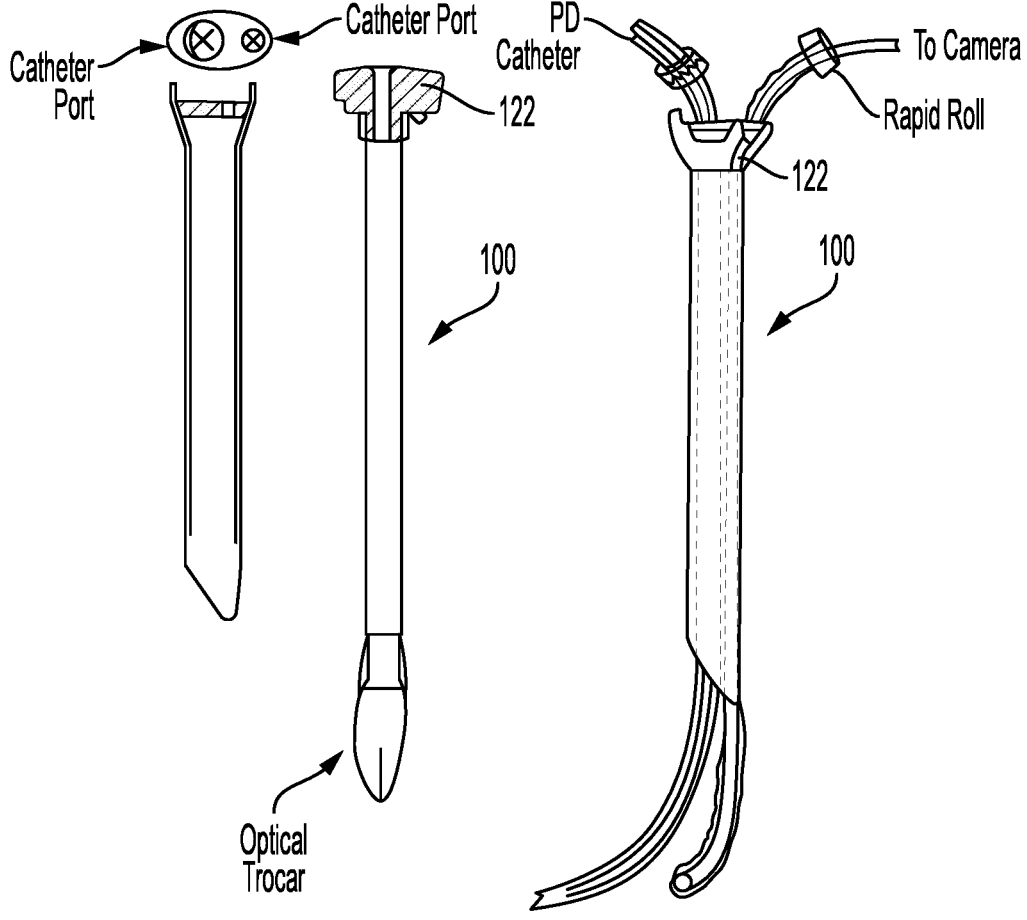
FIGS. 7B and 7C show alternative diagrams of the trocar of FIGS. 1 to 5, according to example embodiments of the present disclosure.
Figure 7C:
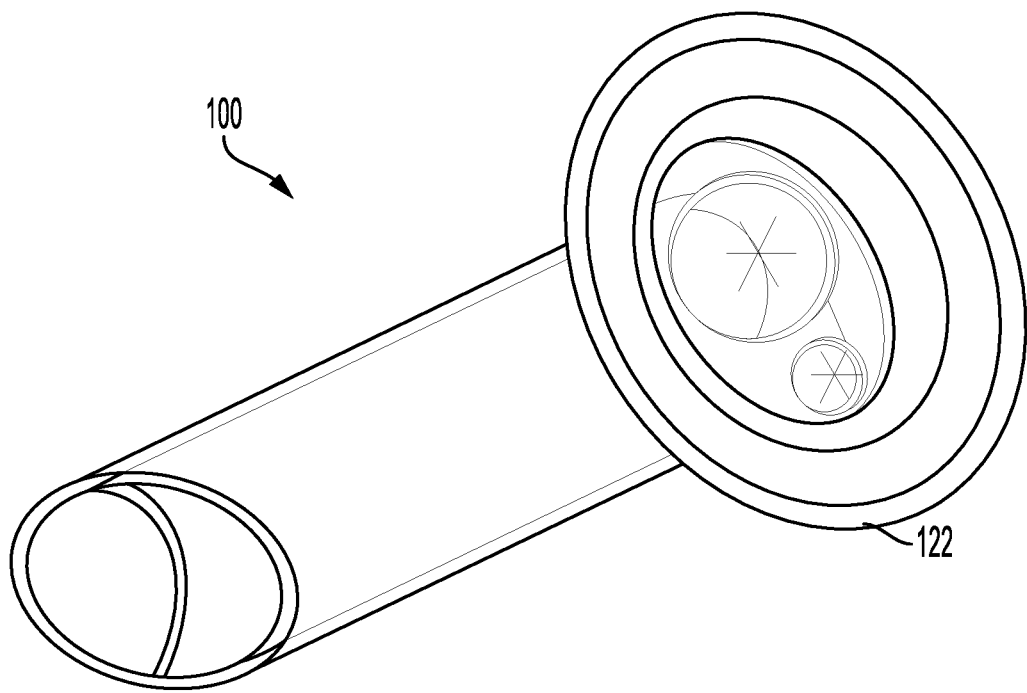

In addition to above, FIGS. 7B and 7C show alternative diagrams of the trocar 100 of FIGS. 1 to 5, according to an example embodiment of the present disclosure. FIGS. 7B and 7C show the trocar 100 having a coupler 122 with locking/coupling mechanisms for a catheter and a camera. Wires or tubing for the catheter and the camera may be wrapped with rapid roll just above the locking/coupling mechanisms to prevent the respective wire or tubing with the rapid roll to pass through the locking/coupling mechanism. The example trocar 100 enables catheter access and camera access through one incision point.

Insufflation Embodiment

In some embodiments, the trocar 100 discussed above in connection with FIGS. 1 to 7C may be used with an insufflation device disclosed herein. Insufflation is a procedure used in minimally invasive surgery that inflates a peritoneal cavity of a patient. In addition to providing more room for placement of a catheter, insufflation increases a backpressure on a peritoneal wall to aid in puncture access. Typical insufflation devices are relatively complex since they are adapted to receive an online supply of gas and provide automated pressure regulation.

Figure 8:
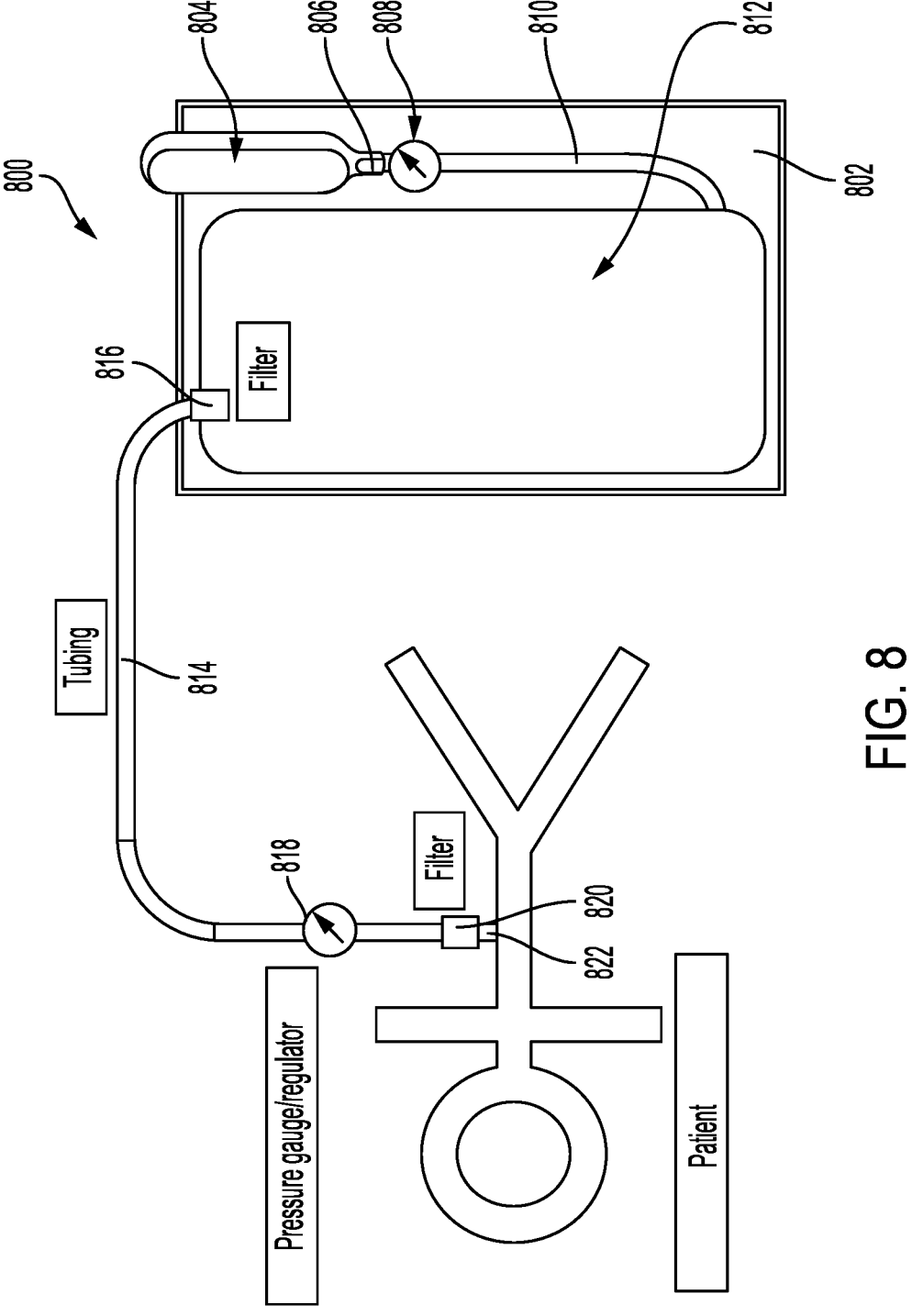
FIG. 8 shows an example insufflation device, according to an example embodiment of the present disclosure.

The insufflation device disclosed herein is configured for use in remote and less developed areas that may not have access to an online supply of gas and hospital management systems. FIG. 8 shows an example insufflation device 800, according to an example embodiment. The insufflation device 800 includes a portable housing 802 and one or more compressed gas cartridges 804. The housing 802 may enclose the cartridges 804 and respective inlet valves. To enable access to the cartridges 804, the housing 802 may include a door. Alternatively, the housing 802 may include an external inlet valve to which an outlet 806 of the compressed gas cartridge 804 may be connected. In some embodiments, the outlet 806 may be connected to an external compressed gas source, such as a compressed gas tank or a gas source provided throughout a medical facility.

The compressed gas cartridges 804 may contain carbon dioxide, atmospheric air, nitrogen, and/or nitrous oxide. The use of cartridges 804 enables portability of the housing 802 to provide insufflation at locations without an online gas source. Further, the cartridges 804 may be relatively easy to obtain from different sources, thereby reducing operating costs of the device 800. In some embodiments, larger gas canisters may be connected via tubing to the valve inlet of the insufflation device 800. Alternatively, the insufflation device 800 may include or be connected to a hand pump to provide pressurized air. Filters within the insufflation device 800 may be used to prevent environmental contaminants from entering a patient's peritoneal cavity.

The example insufflation device 800 of FIG. 8 also includes one or more pressure regulators that control gas pressure. The pressure regulators are used instead of more expensive control electronics. In the illustrated example, a pressure regulator 808 is fluidly coupled to the outlet 806 of the compressed gas container 804. An actuator and gauge of the pressure regulator 808 may be provided on an exterior of the housing 802 to enable operator access.

The example pressure regulator 808 is fluidly coupled to a compliance chamber 812 via a first tube or line 810. The compliance chamber 812 includes a large volume (e.g., 4 to 8 liters depending on child or adult use) relative to the gas to be dispensed. The compliance chamber 812 may be formed from a soft/flexible material or a rigid material. When used with pressure regulators, the relatively large volume minimizes pressure fluctuations from the compressed gas container 804 and/or through the injection of gas into a patient. The compliance chamber 812 is also configured to prevent over pressurization of a patient's peritoneal cavity and helps ensure there is a sufficient volume of gas to maintain a desired pressure (e.g., 10 to 22 cm of $H_2O$) in the peritoneal cavity.

An outlet of the compliance chamber 812 is connected to a second tube or line 814. In some embodiments, a filter 816 may be placed at the outlet of the compliance chamber 812 or between the outlet and the second tube 814. The filter 816 may include a gas particulate filter. In some embodiments, the filter 816 may be disposable. In addition to a filter, the compliance chamber 812 may also include an auto-vent to prevent over pressurization.

The second tube 814 is fluidly connected to a second pressure regulator 818. The two pressure regulators 808 and 818 are configured to regulate a pressure from the cartridge 804 to a physiologically-compatible pressure for a patient's peritoneal cavity. In some embodiments, the first pressure regulator 808 may provide a first pressure downregulation to, for example, two to five times the physiologically-compatible pressure (e.g., from over 1000 pounds per square inch ("PSI") to sub 100 PSI). In these embodiments, the second pressure regulator 818 provides a second step down to the physiologically-compatible pressure. The dual downregulations reduces a pressure gradient through the device 800, thereby reducing the chance of a pressure leak or blow out. In other instances, the pressure regulators 808 and 818 may be set to the same pressure, with the second pressure regulator 818 providing a second pressure check that reduces fluctuations when used with the compliance chamber 812. In some instances, the second pressure regulator 818 may have an internal limit set to a maximum physiologically-compatible pressure for a patient. Alternatively, gauges of the pressure regulator 818 may indicate acceptable patient pressure ranges. In some instances, the pressure regulators 808 and/or 818 may include a controller that emits an audible or visual alarm that is indicative of under or over pressurization.

In embodiments where the second pressure regulator 818 is part of the insufflation device 800, a second filter 820 is connected to an end of the second tube 814. The filter 820 is configured to filter particulates that may enter via venting of the second pressure regulator 818.

The example insufflation device 800 includes an insufflation needle 822 that is fluidly connected to the compliance chamber 812 via the second tube 814. The insufflation needle 822 is configured for placement into a peritoneal cavity of a patient. In some embodiments, the insufflation needle 822 may be placed through the trocar 100 to access the patient's peritoneal cavity.

Figure 9:
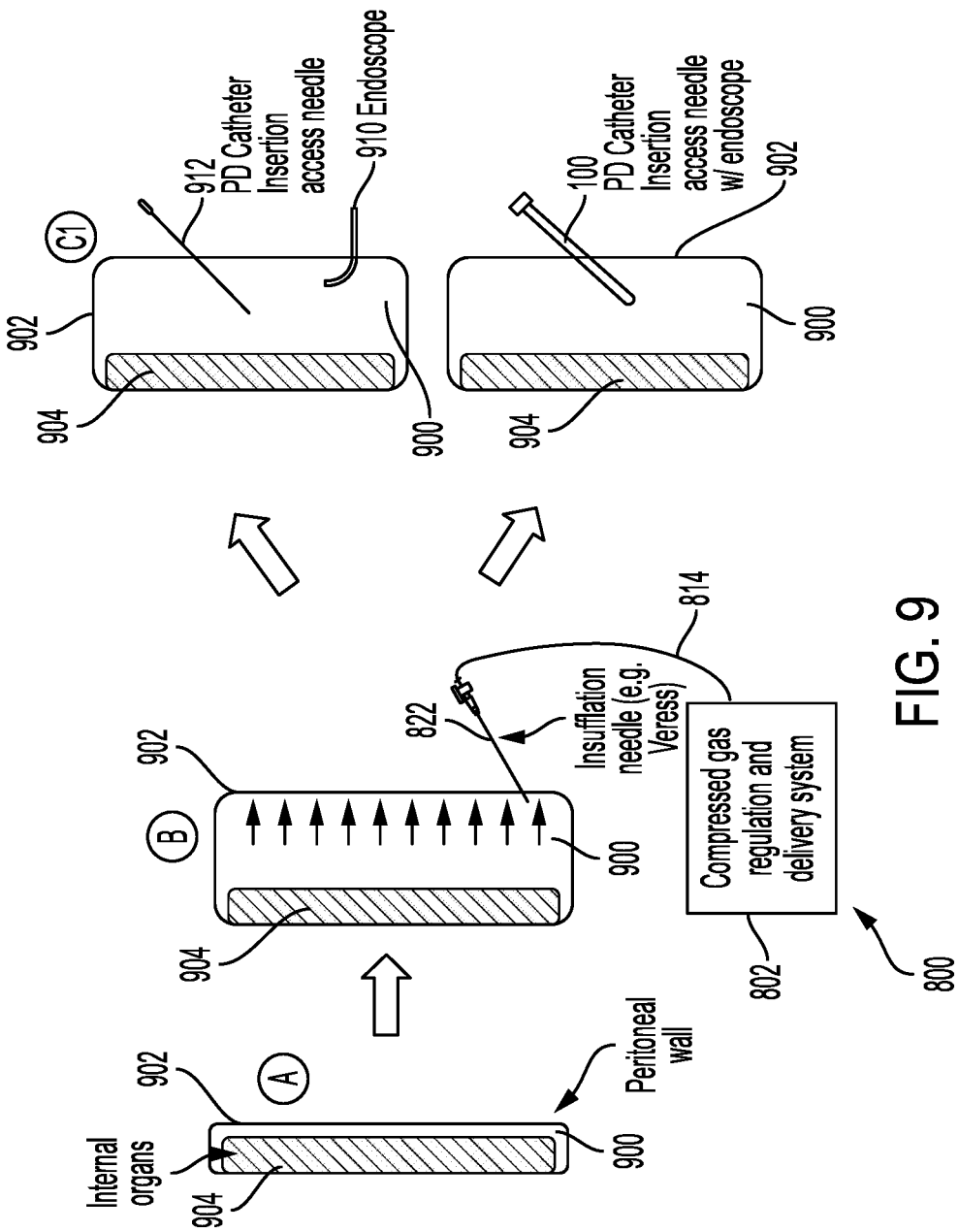
FIG. 9 shows different placements of an insufflation needle for use with the insufflation device of FIG. 8, according to an example embodiment of the present disclosure.

FIG. 9 shows different placements of the insufflation needle 822 for use with the insufflation device 800 of FIG. 8, according to an example embodiment of the present disclosure. Event A shows a peritoneal cavity 900 before insufflation in which a peritoneal wall 902 is relatively close to a patient's internal organs 904. The peritoneal cavity 900 does not have a large volume for placement of a catheter without risking injury to the internal organs 904.

At Event B, the insufflation needle 822 is inserted through the peritoneal wall 902 into the cavity 900. Compressed gas from the insufflation device 800 flows through the tube 814 and the insufflation needle 820 into the peritoneal cavity 900, thereby expanding a volume of the cavity. The increased volume causes the peritoneal wall 902 to move away from the internal organs 904.

In some embodiments, Event C1 occurs. In these embodiments, the insufflation needle 822 is removed and replaced with an endoscope 910 to provide peritoneal cavity visualization. A peritoneal dialysis catheter 912 may then be inserted through the peritoneal wall 902 in to the cavity 900 at a second location. The endoscope 910 enables an operator to determine a preferred placement location for the catheter 912 to perform peritoneal dialysis. It should be appreciated that Event C1 requires two puncture points through the peritoneal wall 902.

In other embodiments, Event C2 occurs. Compared to Event C1, Event C2 only requires a single puncture point through the peritoneal wall 902, thereby reducing chances of fluid leakage from the cavity 900 and patient discomfort. In this example, the trocar 100 discussed above in connection with FIGS. 1 to 7C is inserted through the peritoneal wall 902 into the cavity 900. In this example, the insufflation needle 822 may first be inserted to inflate the peritoneal cavity 900. The insufflation needle 822 is then replaced with the trocar 100, which enables an endoscope and catheter to pass through.

Alternatively, the trocar 100 may be inserted first. After insertion of the trocar 100, the insufflation needle 822 may be inserted through the trocar 100 to inflate the peritoneal cavity 900. After inflation, the insufflation needle 822 is removed and replaced with an endoscope and/or a catheter. After catheter placement, the trocar 100 is removed and peritoneal dialysis begins.

CONCLUSION

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A trocar apparatus comprising:
a conduit having two parallel conduit lumens, the conduit including a first end and a second end;
a head connected to the first end of the conduit, the head including two parallel head lumens that are aligned respectively with the two parallel conduit lumens, the head having a width that is greater than a width of the conduit to prevent the trocar apparatus from slipping into a patient at an insertion location; and
a coupler connected to the head, the coupler including two parallel coupler lumens that are aligned respectively with the two parallel head lumens, the coupler including a coupling mechanism that includes a locking ratcheting mechanism having a straight rectangular bar located at a top of the coupler connected to a wall between the two parallel coupler lumens that is rotatable at a midpoint of a longer axial length of the straight rectangular bar about a center of the coupler between an unlocked position and a locked position to secure via direct contact with the straight rectangular bar, to the coupler, surgical tools located respectively within the two parallel coupler lumens.

2. The trocar apparatus of claim 1, further comprising an obturator having two parallel shafts that are removably inserted through the coupling mechanism and respectively through the coupler lumens, the head lumens, and the conduit lumens, the obturator including an end that is configured to protrude from the second end of the conduit.

3. The trocar apparatus of claim 1, further comprising an obturator having a shaft that is removably inserted through the coupling mechanism and through one of the coupler lumens, one of the head lumens, and one of the conduit lumens, the obturator including an end that is configured to protrude from the second end of the conduit,
wherein the end of the obturator includes at least one of a sharp point, a sharp blade, a blunt tip, or a dilation tip for puncturing into a peritoneal cavity of the patient at the insertion location.

4. The trocar apparatus of claim 3, wherein the obturator is configured for removal from the one of the coupler lumens, the one of the head lumens, and the one of the conduit lumens after insertion of the trocar apparatus into the peritoneal cavity.

5. The trocar apparatus of claim 1, wherein the two parallel conduit lumens are separated from each other via a flexible membrane wall or the two parallel head lumens are separated from each other via the flexible membrane wall.

6. The trocar apparatus of claim 5, wherein an obturator is configured to press against the flexible membrane wall when a shaft of the obturator is inserted through one of the two parallel coupler lumens and one of the two parallel head lumens causing the flexible membrane wall to close or reduce a width of another one of the two parallel head lumens.

7. The trocar apparatus of claim 1, wherein the coupling mechanism of the coupler includes at least one of an elastomeric gasket or seal.

8. The trocar apparatus of claim 1, wherein the surgical tools each include at least one of an insufflation tool, an endoscope, a fluid aspiration tool, an electro-surgery device, a laparoscopic manipulator tool, or a catheter.

9. The trocar apparatus of claim 1, wherein the width of the conduit is between 3 millimeters ("mm") and 15 mm, the width of the head is between 8 mm and 50 mm, and a thickness of a wall of the conduit is between 0.1 mm and 0.8 mm.

10. The trocar apparatus of claim 1, wherein the conduit has a length between 5 centimeters ("cm") and 15 cm.

11. A trocar apparatus comprising:
a conduit having at least one lumen, the conduit including a first end and a second end;
a head connected around an exterior of the conduit at the first end and configured to prevent the trocar apparatus from slipping into a patient at an insertion location, the head including two parallel head lumens; and
a coupler connected to the head, the coupler including two parallel coupler lumens that are aligned respectively with the two parallel head lumens, the coupler including a coupling mechanism that includes a locking ratcheting mechanism having a straight rectangular bar located at a top of the coupler connected to a wall between the two parallel coupler lumens that is rotatable at a midpoint of a longer axial length of the straight rectangular bar about a center of the coupler between an unlocked position and a locked position to secure via direct contact with the straight rectangular bar, to the coupler, surgical tools located respectively within the two parallel coupler lumens.

12. The trocar apparatus of claim 11, wherein the head includes a third parallel head lumen and the coupler includes a third parallel coupler lumen that is aligned respectively with the third parallel head lumen, and wherein the coupler includes the coupling mechanism for each of the two parallel coupler lumens and the third parallel coupler lumen.

13. The trocar apparatus of claim 11, wherein the coupling mechanism of the coupler includes at least one of an elastomeric gasket or a seal.

14. The trocar apparatus of claim 11, wherein the coupling mechanism is configured to connect to a catheter and at least one of an insufflation tool or an endoscope.

* * * * *